(12) United States Patent
Forde et al.

(10) Patent No.: US 11,871,977 B2
(45) Date of Patent: Jan. 16, 2024

(54) CATHETER EXTENSION CONTROL

(71) Applicant: CSA MEDICAL, INC., Lexington, MA (US)

(72) Inventors: Sean Forde, Watertown, MA (US); Sean Arthur McDermott, Weymouth, MA (US); Brian Hanley, Reading, MA (US)

(73) Assignee: CSA MEDICAL, INC., Lexington, MA (US)

( * ) Notice: Subject to any disclaimer, the term of this patent is extended or adjusted under 35 U.S.C. 154(b) by 1096 days.

(21) Appl. No.: 15/158,698

(22) Filed: May 19, 2016

(65) Prior Publication Data

US 2017/0333104 A1 Nov. 23, 2017

(51) Int. Cl.
*A61B 18/02* (2006.01)
*A61B 17/00* (2006.01)
*A61B 90/00* (2016.01)
*A61B 18/00* (2006.01)

(52) U.S. Cl.
CPC .... *A61B 18/02* (2013.01); *A61B 2017/00469* (2013.01); *A61B 2017/00477* (2013.01); *A61B 2018/00166* (2013.01); *A61B 2018/00172* (2013.01); *A61B 2018/00196* (2013.01); *A61B 2018/00541* (2013.01); *A61B 2018/00738* (2013.01); *A61B 2018/00982* (2013.01); *A61B 2018/0212* (2013.01); *A61B 2090/034* (2016.02); *A61B 2090/062* (2016.02); *A61B 2090/0811* (2016.02)

(58) Field of Classification Search
CPC ........ A61B 2090/034; A61B 2090/062; A61B 2090/0811; A61B 2018/00172; A61B 18/02; A61B 2017/00469; A61B 2018/00196; A61B 2018/00738; A61B 2018/00982; A61B 2017/00477; A61B 2018/00541; A61B 2018/00166; A61B 2018/0212

See application file for complete search history.

(56) References Cited

U.S. PATENT DOCUMENTS 3,630,203 A 12/1971 Sellinger
3,782,386 A 1/1974 Barger et al.
4,146,030 A 3/1979 Holroyd
(Continued)

FOREIGN PATENT DOCUMENTS

EP 1588670 10/2005
EP 1985250 10/2008
(Continued)

OTHER PUBLICATIONS

International Search Report (dated Mar. 11, 2014, for PCT/US13/57037 (4 pages).
(Continued)

*Primary Examiner* — Sean W Collins
(74) *Attorney, Agent, or Firm* — GOODWIN PROCTER LLP

(57) ABSTRACT

The present disclosure pertains to devices and methods for diagnosis and treatment of biological tissue in which the tissue is accessed by a catheter through a working channel of an endoscope and in which the degree of extension of a distal tip of the catheter beyond a distal tip of the endoscope is controlled.

19 Claims, 11 Drawing Sheets

(56) References Cited

U.S. PATENT DOCUMENTS

| | | | |
|---|---|---|---|
| 5,520,654 A | 5/1996 | Wahlberg | |
| 5,720,764 A | 2/1998 | Naderlinger | |
| 5,846,235 A | 12/1998 | Pasricha et al. | |
| 5,964,740 A | 10/1999 | Ouchi | |
| 6,126,633 A | 10/2000 | Kaji et al. | |
| 6,143,013 A | 11/2000 | Samson et al. | |
| 6,179,816 B1 | 1/2001 | Mottola et al. | |
| 6,235,019 B1 | 5/2001 | Lehman et al. | |
| 6,237,355 B1 | 5/2001 | Li | |
| 6,287,304 B1 | 9/2001 | Eggers et al. | |
| 6,306,129 B1 | 10/2001 | Little et al. | |
| 6,319,248 B1 | 11/2001 | Nahon | |
| 6,379,337 B1 | 4/2002 | Mohammad M. B. B. S. | |
| 6,461,330 B1* | 10/2002 | Miyagi | A61B 17/3421 604/117 |
| 6,464,716 B1 | 10/2002 | Dobak, III et al. | |
| 6,468,268 B1 | 10/2002 | Abboud et al. | |
| 6,551,309 B1 | 4/2003 | LePivert | |
| 6,599,296 B1 | 7/2003 | Gillick et al. | |
| 6,887,234 B2 | 5/2005 | Abboud et al. | |
| 7,025,762 B2 | 4/2006 | Johnston et al. | |
| 7,331,948 B2 | 2/2008 | Skarda | |
| 7,507,233 B2 | 3/2009 | Littrup et al. | |
| 7,785,289 B2 | 8/2010 | Rios et al. | |
| 7,896,876 B2 | 3/2011 | Kawahara et al. | |
| 7,991,948 B2 | 8/2011 | Levine | |
| 2002/0143323 A1 | 10/2002 | Johnston et al. | |
| 2003/0028182 A1 | 2/2003 | Abboud et al. | |
| 2004/0024392 A1 | 2/2004 | Lewis et al. | |
| 2004/0082905 A1 | 4/2004 | Solar et al. | |
| 2004/0204705 A1* | 10/2004 | Lafontaine | A61B 18/0218 606/23 |
| 2005/0081541 A1 | 4/2005 | Copping | |
| 2005/0228345 A1 | 10/2005 | Yang et al. | |
| 2005/0251111 A1* | 11/2005 | Saito | A61B 17/29 606/1 |
| 2005/0283136 A1 | 12/2005 | Skarda | |
| 2006/0062895 A1 | 3/2006 | Pursley | |
| 2006/0100495 A1 | 5/2006 | Santoianni et al. | |
| 2006/0111613 A1 | 5/2006 | Boutillette et al. | |
| 2007/0112250 A1* | 5/2007 | Kura | A61B 1/31 600/156 |
| 2007/0123852 A1 | 5/2007 | Deem et al. | |
| 2007/0177008 A1 | 8/2007 | Bayer et al. | |
| 2007/0185477 A1 | 8/2007 | Hooven | |
| 2007/0233055 A1 | 10/2007 | Abboud et al. | |
| 2007/0253463 A1 | 11/2007 | Perry et al. | |
| 2008/0275481 A1* | 11/2008 | Scarpone | A61B 17/3421 606/172 |
| 2008/0312644 A1 | 12/2008 | Fourkas et al. | |
| 2009/0078875 A1 | 3/2009 | Rousso et al. | |
| 2009/0157002 A1 | 6/2009 | Dumot et al. | |
| 2009/0192505 A1 | 7/2009 | Askew et al. | |
| 2010/0057065 A1 | 3/2010 | Krimsky | |
| 2010/0057067 A1 | 3/2010 | Baust et al. | |
| 2010/0094216 A1 | 4/2010 | Yue et al. | |
| 2010/0191232 A1 | 7/2010 | Boveda | |
| 2010/0324483 A1 | 12/2010 | Rozenberg et al. | |
| 2011/0004162 A1 | 1/2011 | Tal | |
| 2011/0106074 A1 | 5/2011 | Kunis et al. | |
| 2011/0144524 A1 | 6/2011 | Fish et al. | |
| 2011/0208166 A1 | 8/2011 | Dumot et al. | |
| 2012/0289901 A1* | 11/2012 | Fink | A61B 10/0283 604/117 |
| 2013/0006231 A1 | 1/2013 | Sharma et al. | |
| 2013/0110098 A1 | 5/2013 | Lalonde | |
| 2013/0110099 A1 | 5/2013 | Groves et al. | |
| 2013/0204068 A1 | 8/2013 | Gnanashanmugam et al. | |
| 2013/0218149 A1 | 8/2013 | Braun et al. | |
| 2013/0231651 A1 | 9/2013 | Burr et al. | |
| 2014/0018788 A1 | 1/2014 | Engelman et al. | |
| 2014/0276588 A1* | 9/2014 | Li | A61M 5/46 604/506 |
| 2015/0119868 A1 | 4/2015 | Lalonde et al. | |
| 2015/0126985 A1 | 5/2015 | Newell et al. | |
| 2015/0250524 A1 | 9/2015 | Moriarty et al. | |

FOREIGN PATENT DOCUMENTS

| | | |
|---|---|---|
| EP | 2254637 A1 | 12/2010 |
| GB | 2456425 A | 7/2009 |
| JP | H1170170 A | 3/1999 |
| JP | 2002153475 | 5/2002 |
| JP | 2008531139 A | 8/2008 |
| JP | 2009090003 | 4/2009 |
| JP | 2013526302 A | 6/2013 |
| WO | 9204872 A1 | 4/1992 |
| WO | 9915093 A1 | 4/1999 |
| WO | 0101049 A1 | 1/2001 |
| WO | 0207625 A2 | 1/2002 |
| WO | 0211638 A1 | 2/2002 |
| WO | 2009082433 A2 | 7/2009 |
| WO | 2009140067 A1 | 11/2009 |
| WO | 2011140585 A1 | 11/2011 |
| WO | 2012006408 A1 | 1/2012 |
| WO | 2013062846 A1 | 5/2013 |
| WO | 2014137383 A1 | 9/2014 |
| WO | 2016010568 A1 | 1/2016 |

OTHER PUBLICATIONS

T J Lynch, Polyimide Tubing: Dispelling the Myths, Microlumen, http://www.microlumen.com/news/industry-news/18-polyimide-tubing-dispelling-the-myths.

International Search Report and Written Opinion (dated Nov. 14, 2017), for PCT/US16/33262 (28 pages).

International Search Report and Written Opinion for PCT/US2019/018829, dated May 23, 2019, 9 pages.

International Search Report and Written Opinion for International Patent Application No. PCT/US17/45217 dated Oct. 23, 2017, 10 pages.

\* cited by examiner

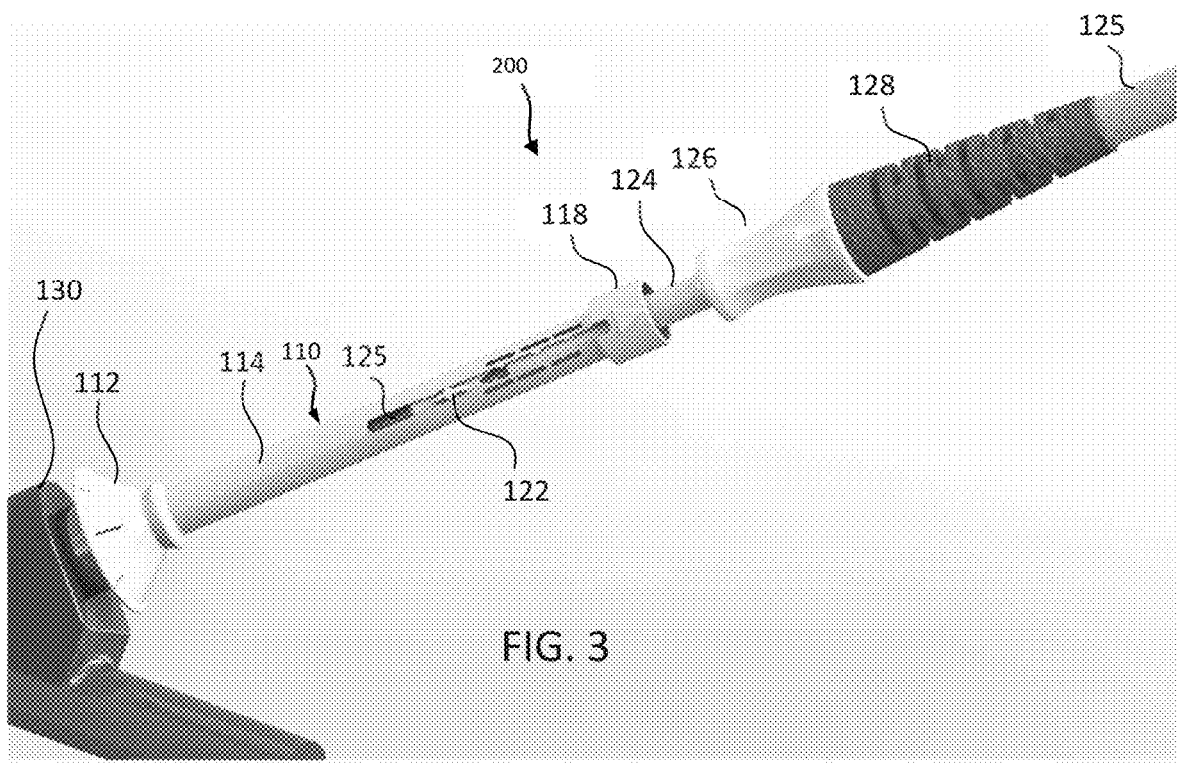
FIG. 3
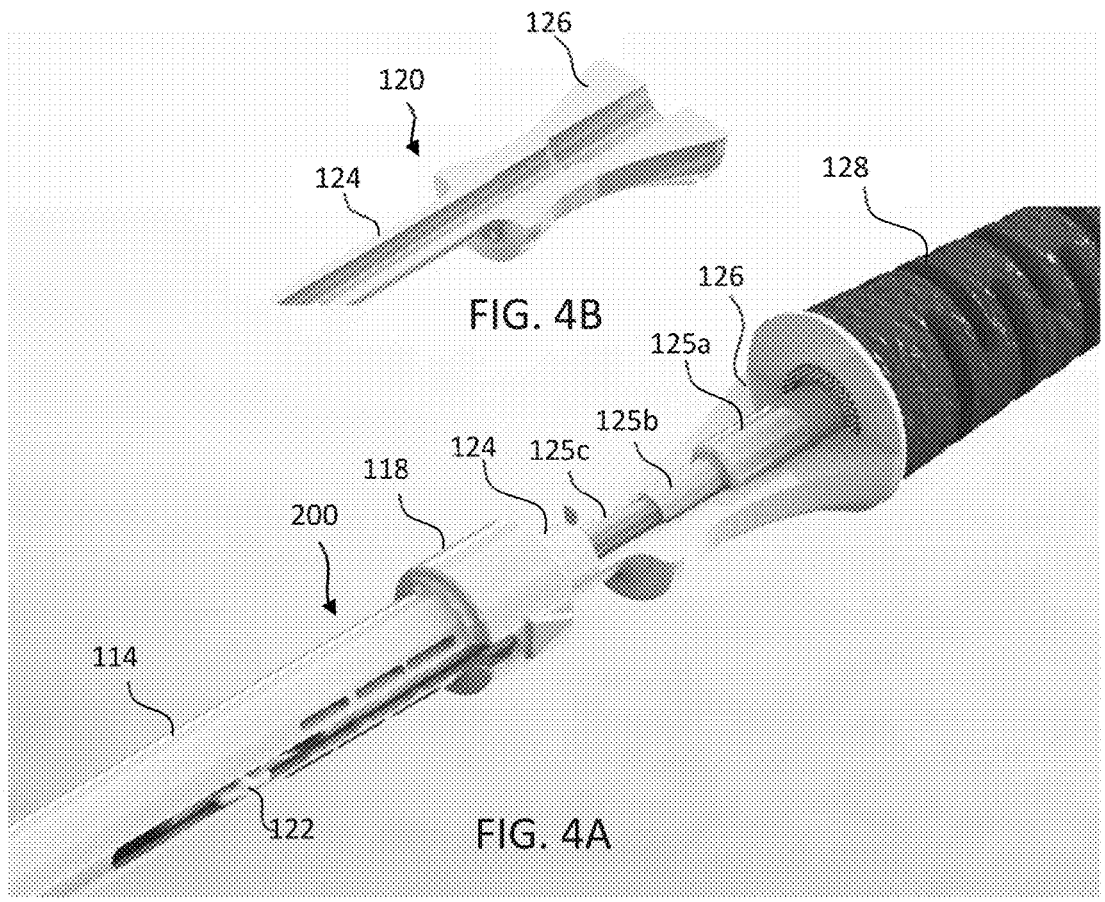
FIG. 4B
FIG. 4A

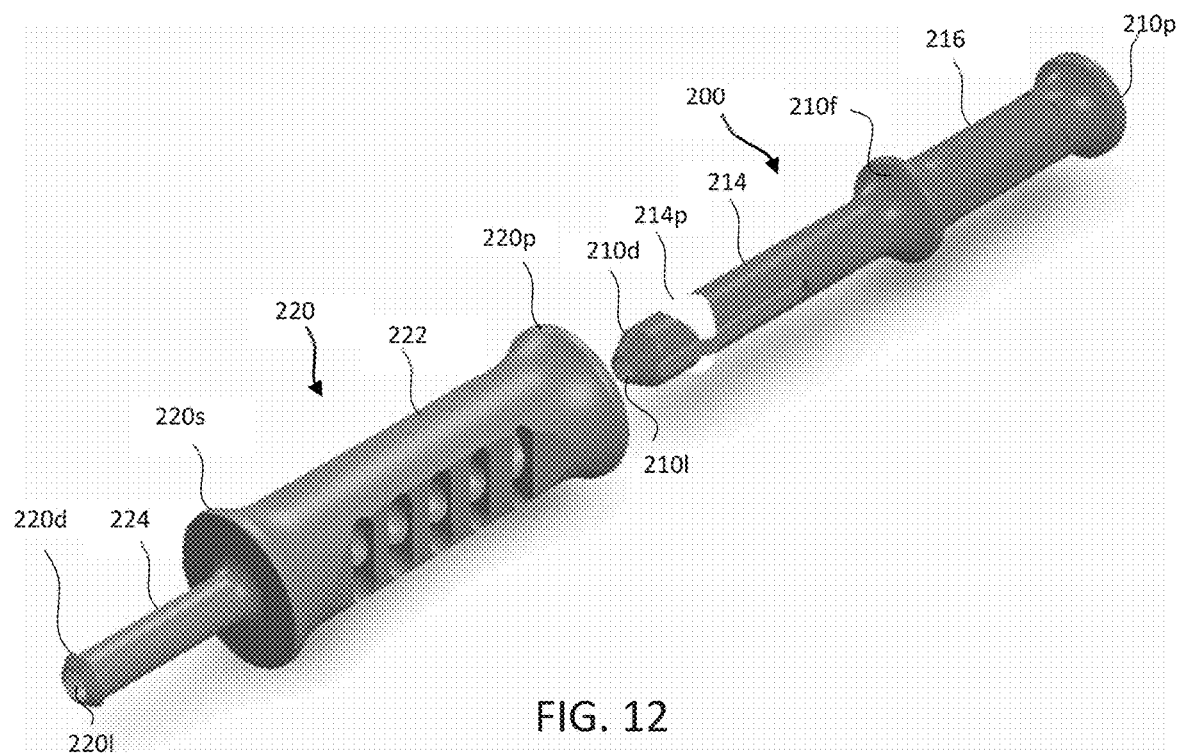
FIG. 12
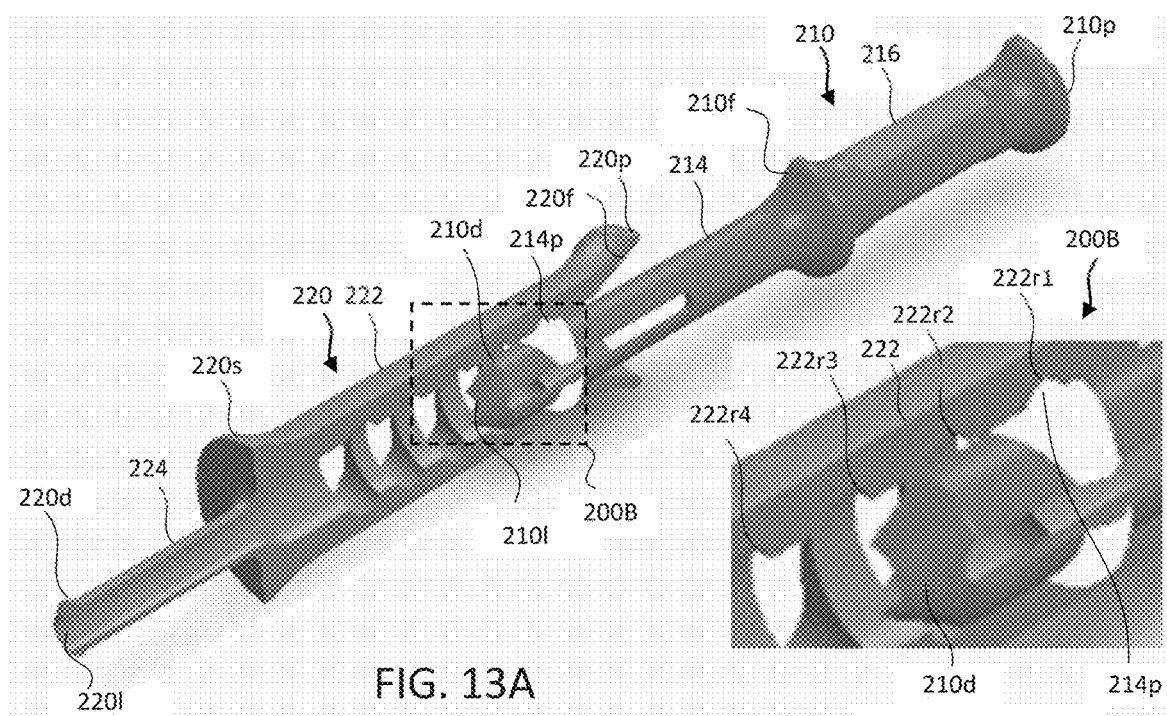
FIG. 13A
FIG. 13B

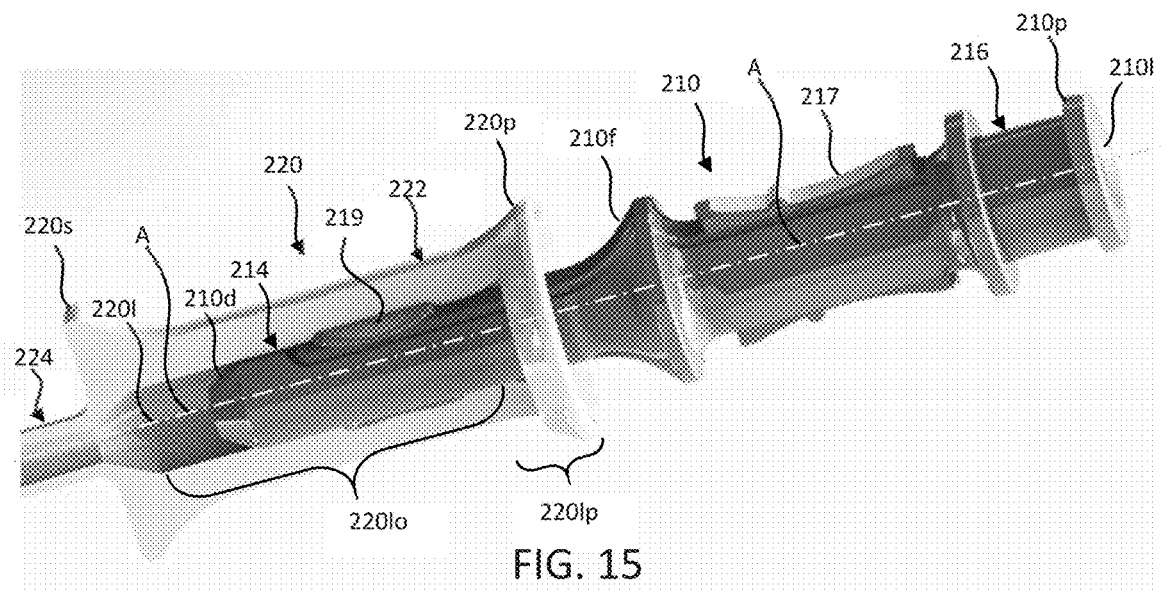
FIG. 15
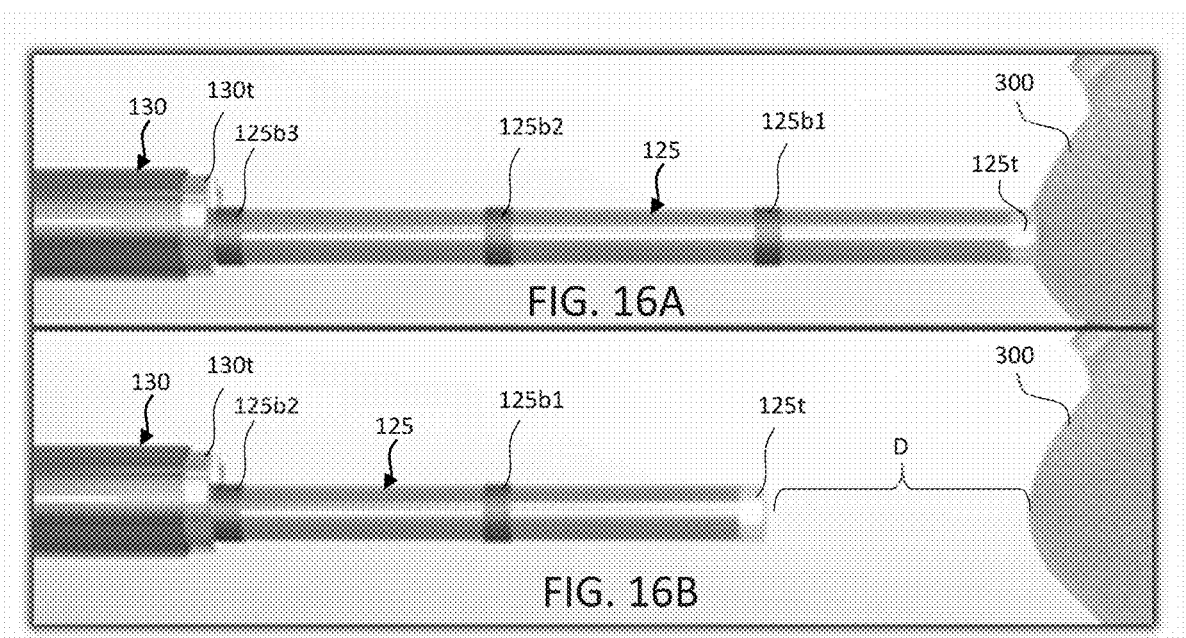
FIG. 16A
FIG. 16B

CATHETER EXTENSION CONTROL

FIELD OF THE DISCLOSURE

The present disclosure relates generally to devices, systems and methods wherein a catheter is introduced to a site within a subject via another device, and more particularly, to devices and methods for diagnosis and treatment of biological tissue in which the tissue is accessed by a catheter through a working channel of an endoscope.

BACKGROUND

Endoscopes are employed in a wide variety of medical procedures. Examples of commonly employed endoscopes include the following, among others (listed along with the area or organ typically viewed): arthroscopes (joints), bronchoscopes (trachea and bronchi of the lungs), colonoscopes (colon and large intestine), colposcopes (vagina and cervix), cystoscopes (bladder), esophagoscopes (esophagus), gastroscopes (stomach and duodenum), laparoscopes (stomach, liver, or other abdominal organ, including female reproductive organs), laryngoscopes (larynx), neuroendoscopes (brain), proctoscopes (rectum and sigmoid colon), sigmoidoscopes (sigmoid colon), and thoracoscopes (pleura covering the lungs and structures covering the heart).

In various medical procedures it is desirable to introduce a catheter to a site within a subject for purposes of diagnosis and/or treatment of biological tissue at the site. Examples of such catheters include tissue ablation catheters and drug delivery catheters, among others. Tissue ablation refers to the removal or destruction of tissue, or of tissue functions. Appropriate target tissue for ablation may include, for example, cancerous or precancerous lesions, tumors (malignant or benign), damaged epithelium, fibroses and any other healthy or diseased tissue for which tissue ablation is desired.

Cryoablation is a relatively recent technique in which tissue ablation is conducted by freezing a target tissue of interest. Cryoablation may be performed by using a system that sprays low pressure cryogen on the target tissue. Such systems are often referred to as cryosurgery systems, cryosurgery spray systems, cryogen spray systems, and cryospray systems, among other terms. As used herein, "cryogen" refers to any fluid (e.g., gas, liquefied gas or other fluid known to one of ordinary skill in the art) that has a sufficiently low boiling point to allow for therapeutically effective cryotherapy and is otherwise suitable for cryogenic surgical procedures. For example, acceptable fluids may have a boiling point below approximately negative (−) 150° C. The cryogen may be liquefied nitrogen, as it is readily available. Other fluids such as argon and air may also be used. Additionally, liquid helium, liquid oxygen, liquid nitrous oxide and other cryogens can also be used.

During typical operation of a cryosurgery system, a clinician, physician, surgeon, technician, or other operator (collectively referred to as "operator" herein), sprays cryogen on the target tissue via a delivery catheter. The spray of cryogen causes the target tissue to freeze or "cryofrost." The physician may target the cryospray visually utilizing endoscopy, bronchoscopy, pleuroscopy, or other video assisted device or scope.

SUMMARY OF THE DISCLOSURE

In the course of various procedures, it may be desirable to introduce a catheter to a site for treatment or diagnosis. In certain of these procedures, catheter access to the treatment or diagnosis site may be provided via a working channel of an endoscope. In such procedures, it may be desirable to provide improved control of a distance by which a distal tip of the catheter extends from a distal tip of the endoscope, for example, by improving the resistance to relative movement between the endoscope and catheter during treatment and/or navigation and, with regard to cryosurgery systems, by ensuring that the catheter is extended from the distal tip of the endoscope by a distance sufficient to avoid the formation of obstructive amounts of frost on a lens of the endoscope, among other improvements.

The present disclosure provides devices, systems and methods that allow for precise positioning of a catheter tip during the course of treatment of tissue within a subject. The devices, systems and methods pertain to the use of an endoscope for the navigation and visualization of the target tissue, and the use of a catheter to diagnose and/or treat such target tissue after extending a distal tip of the catheter to one or more predetermined distances from a distal tip of the endoscope. In certain embodiments, the catheter may be part of a cryogen spray system in which the catheter is connected to a console that houses and delivers cryogen fluid to the catheter.

BRIEF DESCRIPTION OF THE DRAWINGS

FIG. 3 is a perspective view of a catheter extension control assembly, in accordance with an embodiment of the present disclosure.

FIGS. 4A and 4B are partial cutaway views of the catheter extension control assembly of FIG. 3.

FIG. 12 is a perspective view of a portion of the catheter extension control assembly, in accordance with another embodiment of the present disclosure.

FIG. 13A is a cutaway of the portion of the catheter extension control assembly shown in FIG. 12. FIG. 13B is an enlarged view of a portion of FIG. 13A.

FIG. 15 is a perspective view of a portion of the catheter extension control assembly, in accordance with yet another embodiment of the present disclosure.

FIG. 16A is a side view showing a distal portion of a catheter extension control assembly in a position wherein a distal tip of the catheter is touching tissue, in accordance with an embodiment of the present disclosure.

FIG. 16B is a side view showing a distal portion of a catheter extension control assembly in a position wherein a distal tip of the catheter is withdrawn from tissue, in accordance with an embodiment of the present disclosure.

DETAILED DESCRIPTION

Figure 1:
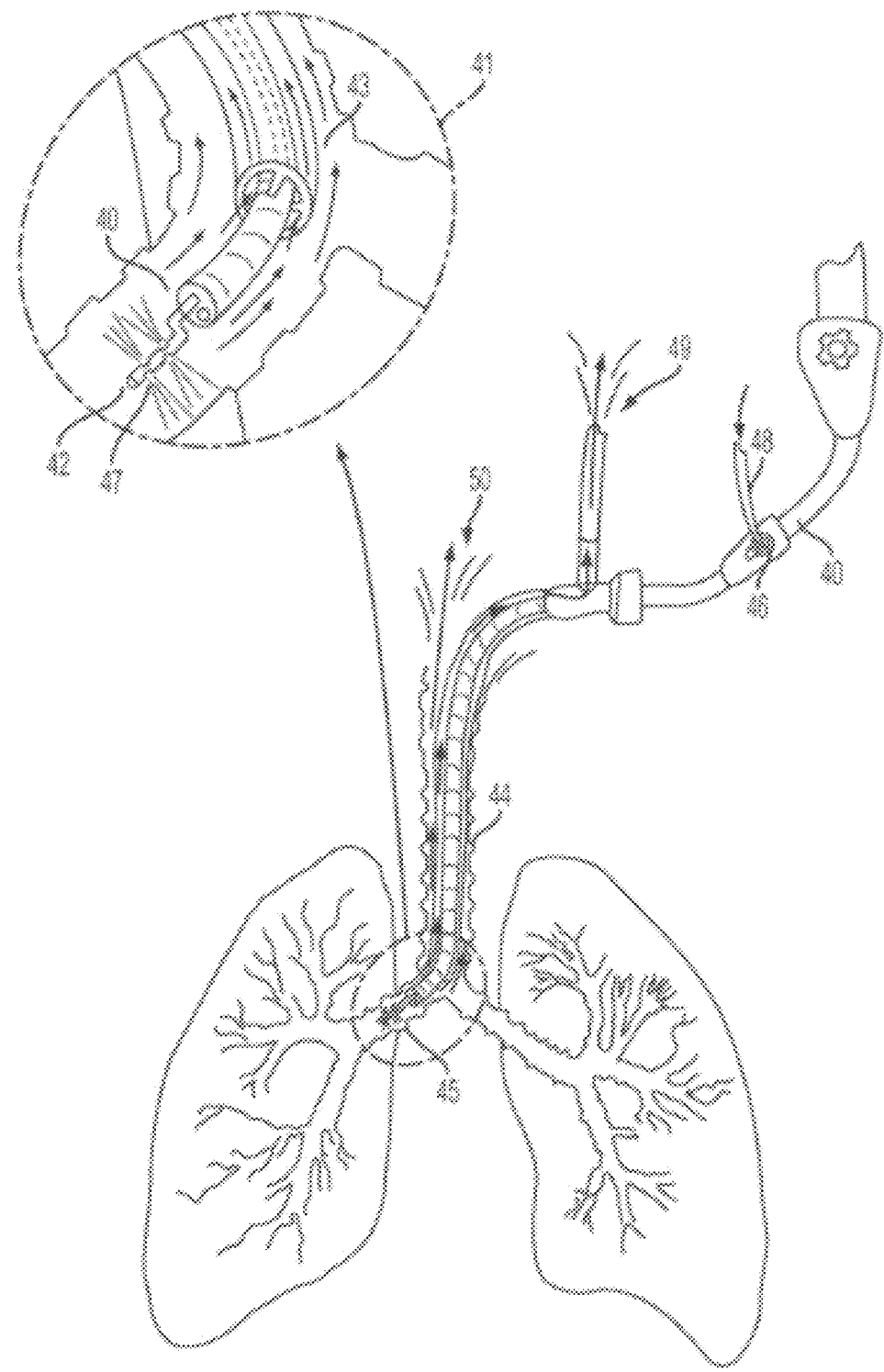
FIG. 1 is a perspective view of a portion of a cryosurgery system, in accordance with an embodiment of the present disclosure.

FIG. 1 is a perspective view of a portion of a cryosurgery system 41 having a cryogen delivery apparatus 42. Cryosurgery system 41 comprises a bronchoscope 40 and a catheter tip 42 exiting its working channel. As shown, bronchoscope 40 may be positioned in the trachea 44, or bronchi—such as the principle bronchi 45 of patient. The catheter 48 is placed in the working channel lumen 46 of the scope 40 and exits the working channel at the distal tip of the scope. Cryogen delivery apparatus 42 comprises a radial spray cryogen delivery catheter at distal end 42, and one or more holes 47. After insertion of the cryogen delivery apparatus into the patient, cryogen is provided to cryogen delivery catheter 48 from a cryogen source. Catheter distal end with one or more holes 42 causes the cryogen to be sprayed on the target tissue via the hole(s) 42. A gas egress tube 43 that surrounds the scope may be utilized to provide additional means to evacuate the treatment area of the cryogenic gas out of the patient 49. Passive lumen egress 50 is also present via the management of the airway to ensure proper venting during the procedure. In certain beneficial embodiments, the cryogen delivery catheter 48 may include (1) a bayonet and hub for attachment to the console at its proximal end, (2) a layered polyimide and stainless steel braided shaft to minimize kinking and breaking, (3) insulation to protect the user from cold, (4) a strain relief to help prevent kinking when torqued by users and (5) an atraumatic tip at its distal end to prevent damage to tissue, as described in U.S. Patent Pub. No. 2015/0066005 to Wei Li Fan et al.

In procedures where a catheter is advanced to a site in a subject through an endoscope, FIG. 1 representing one specific example of such a procedure, it is beneficial for the operator to able to position the catheter tip at one or more predetermined distances from the distal tip of the endoscope and to maintain the catheter tip at such a position, if desired.

In accordance with the present disclosure, a variety of devices, systems and methods are provided for doing so.

Endoscopes useful for such procedures may be of any size suitable for the site being accessed. In certain embodiments, an endoscope having one or more one or more optical (e.g., fiber optic) and/or electronic (e.g., camera, led, etc.) elements may be provided in order to project light from a distal tip of the endoscope onto the site and to transmit an image of the site back from the distal tip, for example, to a monitor or a microscope, where the procedure can be visualized. Assisted by this visualization, an operator is able to perform diagnostic and/or therapeutic procedures via an inserted catheter beyond a distal end of the endoscope. Examples of endoscopes for use in conjunction with the present disclosure include arthroscopes bronchoscopes, colonoscopes, colposcopes, cystoscopes, esophagoscopes, gastroscopes, laparoscopes, laryngoscopes, neuroendoscopes, proctoscopes, sigmoidoscopes, and thoracoscopes, among others.

Catheters useful for such procedures vary widely and may also be of any size suitable for the site being accessed. Although cryogen delivery catheters are specifically described herein, the present disclosure is not so limited and applies to any catheter used in conjunction with any type of endoscope.

Figure 2A:
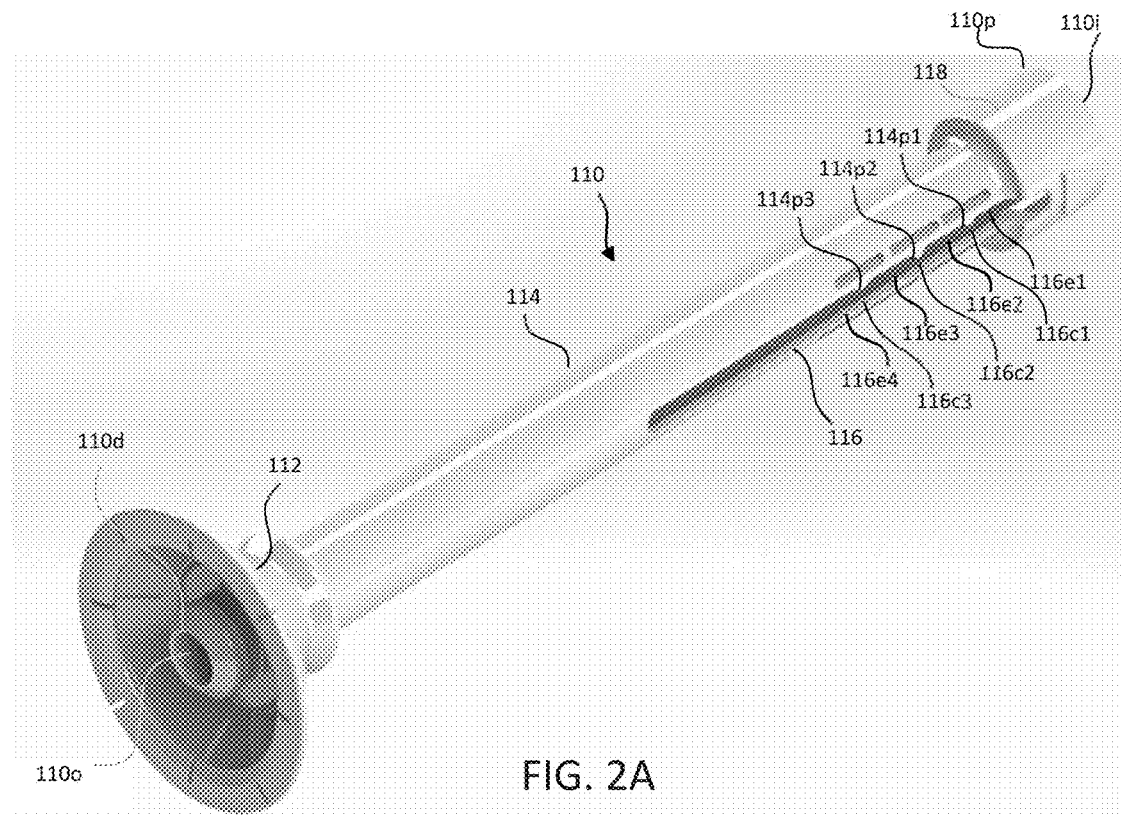
FIG. 2A is a perspective view of a tubular member, in accordance with an embodiment of the present disclosure.

Turning now to FIG. 2A, a tubular member 110 (also referred to as an introducer) is shown therein, which comprises an inlet 110i, an outlet 110o, a proximal end 110p, a distal end 110d, and a lumen extending between the inlet 110i, and outlet 110o. Tubular member 110 is configured for engagement with a working channel of an endoscope. For this purpose, tubular member 110 may be provided with an attachment feature 112, which can be directly attached to a working channel of an endoscope, for example, as shown. In other embodiments, tubular member 110 may be attached to an additional component that is configured for attachment to a working channel of an endoscope, for instance, a biopsy cap.

The tubular member 110 comprises a body portion 114 and a widened portion adjacent inlet 110i, specifically, a cuff portion 118 in the embodiment shown, which eases introduction of a catheter assembly into the tubular member 110 as described in more detail below. A slot 116, which extends through a sidewall of the tubular member 110, is formed in the proximal end of the body portion 114 and extends into the widened portion 118, where it serves as a keyhole feature for receiving an extension feature, as described in more detail below. Protrusions 114p1, 114p2, 114p3 extend from the body portion into the slot, forming regions of constricted slot width 116c1, 116c2, 116c3 in slot 116, which lie between regions of expanded slot width 116e1, 116e2, 116e3, 116e4 in slot 116.

In some embodiments, the tubular member 110 may be designed to provide strain relief. For example, although not illustrated, in order to provide strain relief, a spiral cut may be provided in a sidewall of the body portion 114 for instance, in the region between the slot 116 and attachment feature 112, among various other possible approaches.

The tubular member 110 of FIG. 2A may be used in conjunction with an assembly that includes an inner member comprising a catheter and an extension feature extending radially outward from an axis of the catheter, in which case the inner member is positioned within the tubular member 110 such that the extension feature slidably fits within the slot 116 of the tubular member 110.

In some embodiments, such an inner member may comprise, for example, a catheter with an extension feature extending from and integrated into a sidewall of the catheter.

Figure 2B:
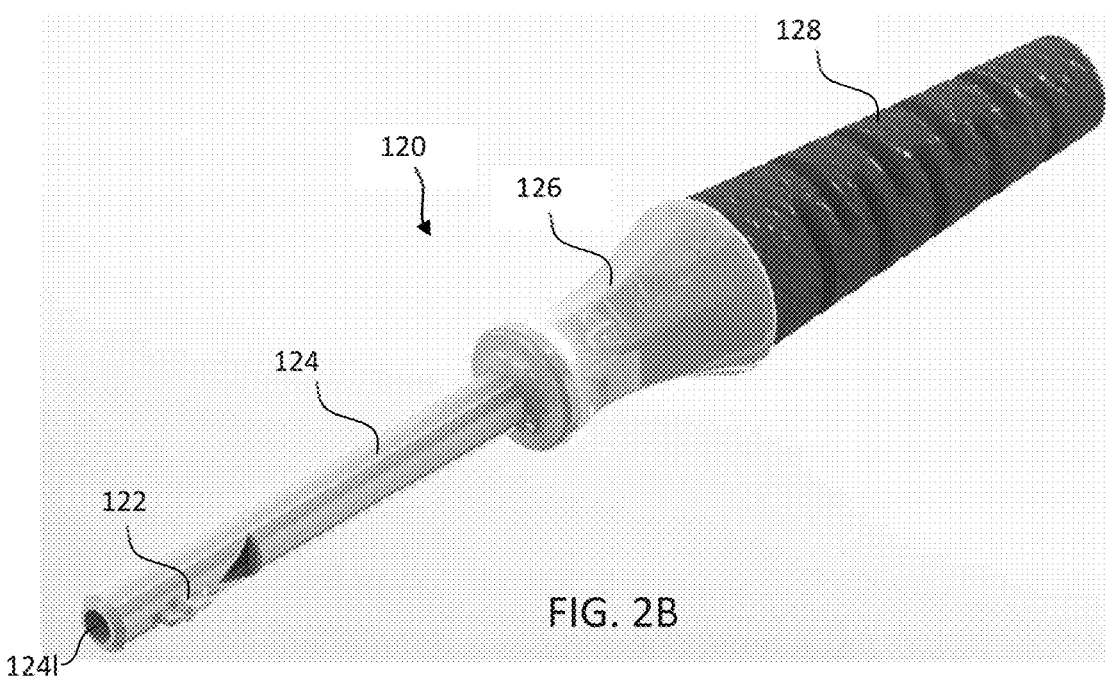
FIG. 2B is a perspective view of a catheter handle assembly, in accordance with an embodiment of the present disclosure.

In other embodiments, such an inner member may comprise, for example, an assembly which includes a mechanism whereby an extension feature is fixed at a predetermined position along a length of the catheter. One example of such a mechanism is a catheter handle assembly 120, illustrated in FIG. 2B, which comprises a hollow shaft portion 124 having a lumen 124l and an extension feature 122. A catheter (not shown) may be passed through the lumen 124l. The hollow shaft portion 124 in the embodiment shown may be coupled to a tapered region 126 and/or a strain relief component 128. The tapered region 126 may be further connected to a strain relief component 128, which along with tapered region 126, serves a handle function. Although not shown, in use, a catheter will pass through the lumen 124l of the catheter handle assembly 120 (from right-to-left in the image shown). While the catheter handle assembly 120 may be in the form of an assembly of separate components in some embodiments, in other embodiments two, three, or all of the hollow shaft portion 124, extension feature 122, tapered region 126 and strain relief component 128 may be integrated into a single component.

As seen from the catheter extension control assembly 200 illustrated in FIG. 3, a catheter 125 may be attached to and extend through the strain relief component 128, tapered region 126 and shaft portion 124 of the catheter handle assembly 120. As noted elsewhere, the catheter may be any of a wide range of catheters, which in certain embodiments may include cryospray catheters. The catheter 125 further extends through the tubular member 110 and into a working channel of an endoscope 130. The extension feature 122 is configured to slidably fit within the elongated slot 116 of the tubular member 110. Because the extension feature 122 is wider than the regions of constricted slot width 116c1, 116c2, 116c3, the regions of constricted slot width act as stops with regard to the advancement of the extension feature 122 (and thus the catheter that is attached to the extension feature 122). By forming the tubular member 110 from a material that has appropriate elasticity, the extension feature 122 can be moved by an operator, through application of a suitable force, from the first region of expanded slot width 116e1, through the first region of constricted slot width 116c1 (which acts as a first stop, until sufficient force is applied), and into the second region of expanded slot width 116e2. Subsequently, the extension feature 122 can be moved from the second region of expanded slot width 116e2, through the second region of constricted slot width 116c2 (which acts as a second stop, until sufficient force is applied) and into the third region of expanded slot width 116e3. Thereafter, the extension feature 122 can be moved by from the third region of expanded slot width 116e3 through the third region of constricted slot width 116c3 (which acts as a third stop, until sufficient force is applied) and into the fourth and final region of expanded slot width 116e4.

As the extension feature 122 is advanced within the slot 116, the catheter 125 is advanced within the endoscope 130. The length of extension of the catheter 125 from the endoscope 130 is determined by the position of the regions of constricted slot width. FIGS. 5A-5D illustrate the proximal end of the system, including (a) the slot 116 of the tubular member 110 and (b) the shaft portion 124 with extension feature 122, tapered region 126 and strain relief component 128 of the catheter handle assembly 120. FIGS. 5A-5D also illustrate the distal end of the system, including (a) a distal tip 130t of endoscope 130 and (b) a distal tip 125t and first marker band of 125b1 of catheter 125. Although not shown, in further embodiments, visually identifiable marks may be placed on a proximal end of the catheter 125 outside of the endoscope 130, as an additional or alternative means of controlling and/or monitoring extension.

Figure 5A:
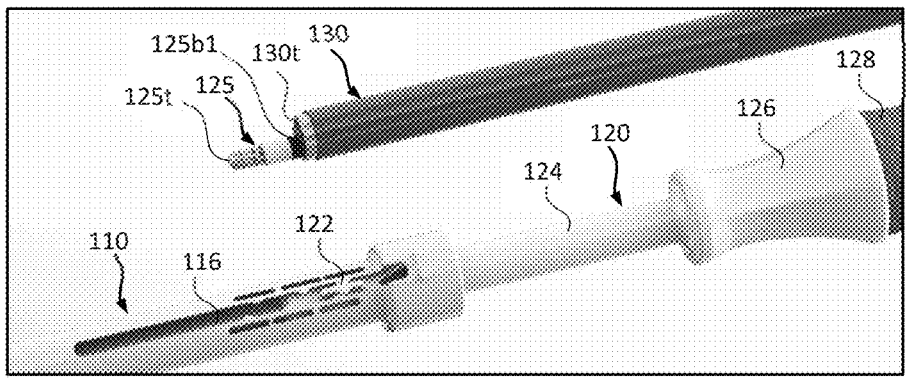
FIG. 5A shows perspective views of proximal and distal portions of a catheter extension control assembly in a first position, in accordance with an embodiment of the present disclosure.

In FIG. 5A, the catheter handle assembly 120 has been moved relative to the tubular member 110 to a point where the extension feature 122 has been moved against the first region of constricted slot width 116c1 (see FIG. 2A), which acts as a first stop, corresponding to a position where the first marker band 125b1 begins to emerge from the distal tip 130t of endoscope 130.

Figure 5B:
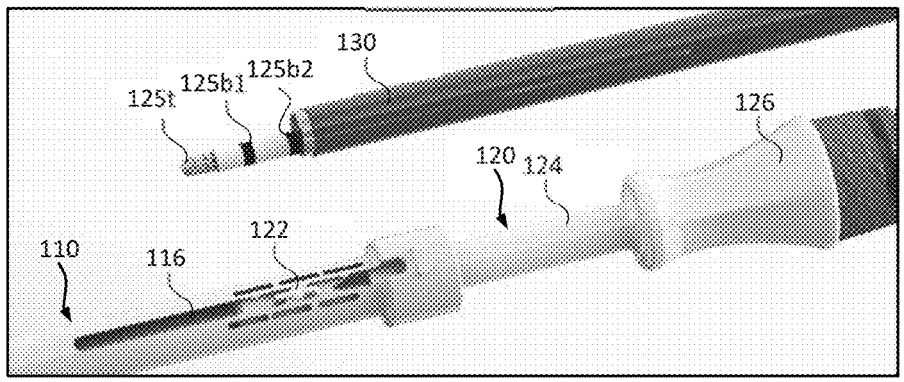
FIG. 5B shows perspective views of proximal and distal portions of a catheter extension control assembly in a second position, in accordance with an embodiment of the present disclosure.

By applying a sufficient force, the extension feature can be moved through the first region of constricted slot width 116c1, into and through the second region of expanded slot width 116e2, and against the second region of constricted slot width 116c2 (see FIG. 2A), which acts as a second stop. As seen in FIG. 5B, the second stop corresponds to a position where the second marker band 125b2 begins to emerge from the distal tip 130t of endoscope 130.

Figure 5C:
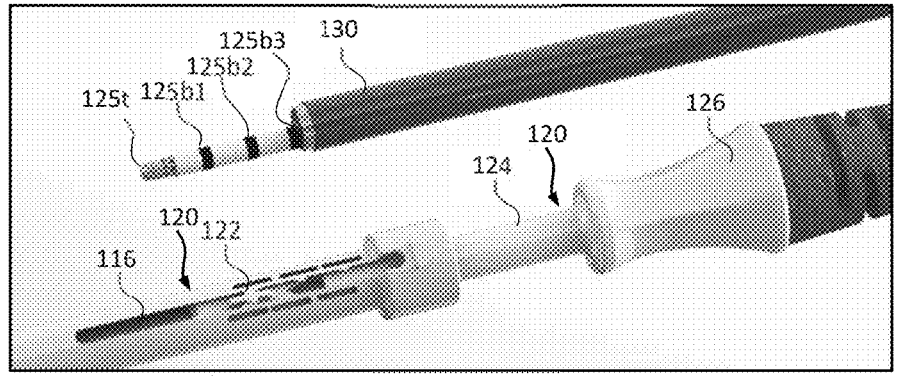
FIG. 5C shows perspective views of proximal and distal portions of a catheter extension control assembly in a third position, in accordance with an embodiment of the present disclosure.

By again applying a sufficient force, the extension feature 122 can be moved through the second region of constricted slot width 116c2, into and through the third region of expanded slot width 116e3, and against the third region of constricted slot width 116c3, which acts as a third stop. As seen in FIG. 5C, the third stop corresponds to a position where the third marker band 125b3 begins to emerge from the distal tip 130t of endoscope 130.

Figure 5D:
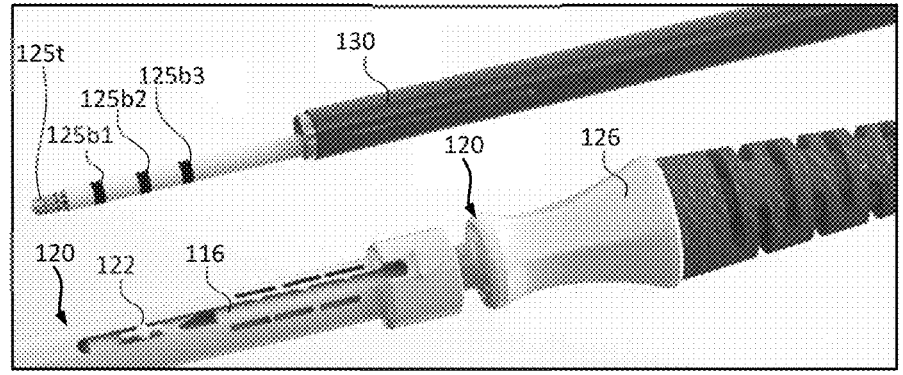
FIG. 5D shows perspective views of proximal and distal portions of a catheter extension control assembly in a fourth position, in accordance with an embodiment of the present disclosure.

Finally, by yet again applying a sufficient force, the extension feature 122 can be moved through the third region of constricted slot width 116c3, into and through the fourth region of expanded slot width 116e4, and up to a point of maximum extension of the catheter handle assembly 120 relative to the tubular member 110, as seen in FIG. 5D.

Figure 5E:
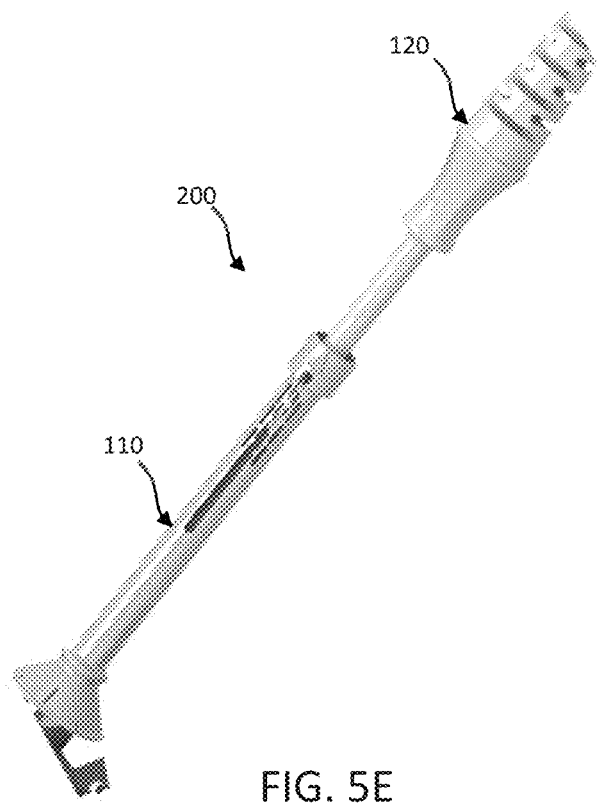
FIGS. 5E and 5F are perspective views further illustrating movement between a catheter handle assembly and a tubular member of a catheter extension control assembly, in accordance with the present disclosure.
Figure 5F:
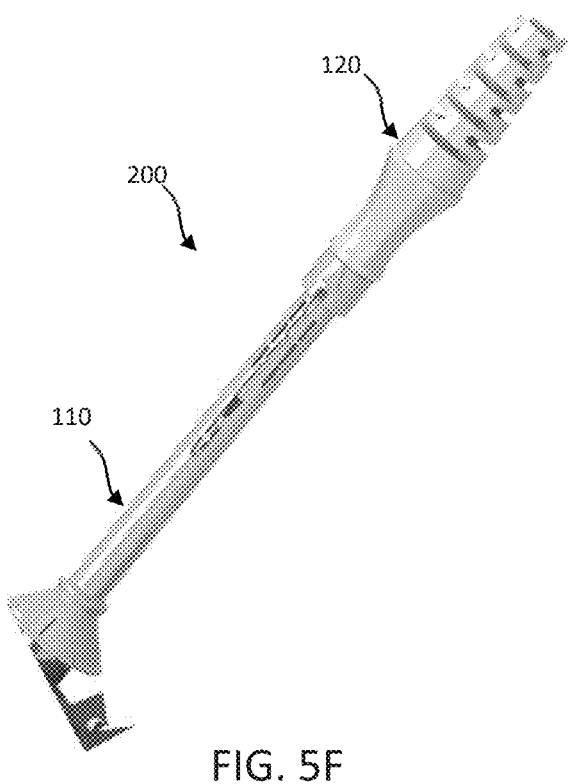

FIGS. 5E and 5F further illustrate movement of the catheter handle assembly 120 relative the tubular member 110 of the catheter extension control assembly 200.

With reference now to FIGS. 16A and 16B, during use, catheter extension control assemblies in accordance with the present disclosure may be used to perform a number of operations, including withdrawal and/or advancement of a catheter tip by a predefined distance. In this regard, FIG. 16A is a side view showing a distal portion of a catheter extension control assembly including an endoscope 130 having an endoscope tip 130t and a catheter 125 having a catheter tip 125t and marker bands (marker bands 125b1, 125b2, 125b3 are shown). In FIG. 16A, the catheter distal tip 125t is in contact with tissue 300. In FIG. 16B, on the other hand, the catheter distal tip 125t is pulled back from contact with the tissue 300. Catheter extension control assemblies in accordance with the present disclosure are useful for this task, for example, as the catheter tip 125t may be reliably and reproducibly retracted by a known distance D (e.g., 1 cm, among other distances) from the tissue 300. FIGS. 4A and 4B show further construction details of the catheter extension control assembly, including a cutaway view of a proximal part of the shaft portion 124 and the tapered portion 126 of the catheter handle assembly 120 as well as three catheter portions 125a, 125b and 125c of varying diameter that are positioned in the interior of the catheter handle assembly 120.

Figure 6:
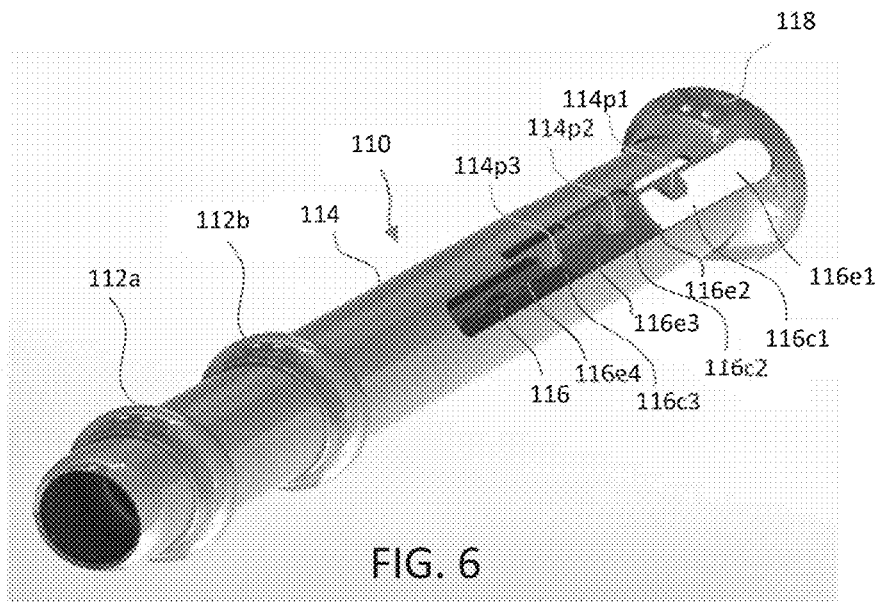
FIGS. 6 and 7 are perspective view of tubular members, in accordance with two embodiments of the present disclosure.

An additional embodiment of a tubular member 110 in accordance with the present disclosure is shown in FIG. 6 and includes a body portion 114, flared widened portion 118, attachment features 112a and 112b, and a slot 116 formed in a proximal end of the body portion 114 which extends into the widened portion 118. Protrusions 114p1, 114p2, 114p3 extend from the body portion 114 into the slot 116, forming regions of constricted slot width 116c1, 116c2, 116c3 that lie between regions of expanded slot width 116*e*1, 116*e*2, 116*e*3, 116*e*4, with the regions of constricted slot width 116*c*1, 116*c*2, 116*c*3 acting as stops for the catheter handle assembly 120 (not shown) when inserted into the tubular portion 110 in a fashion analogous to that described in conjunction with FIGS. 5A-5D.

Figure 7:
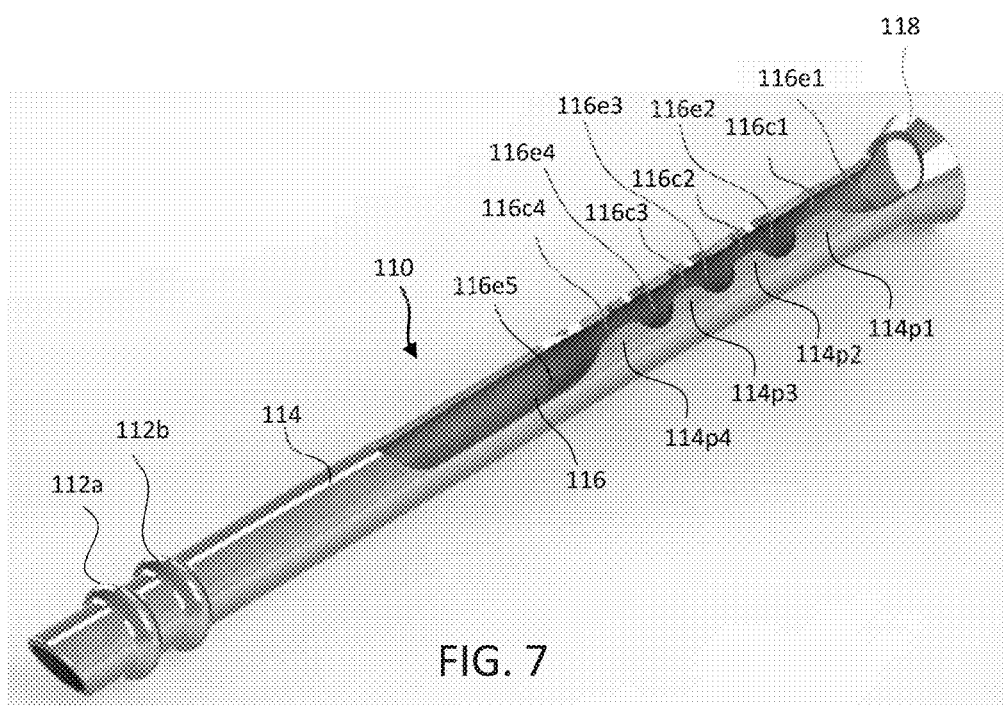

Yet another embodiment of a tubular member 110 in accordance with the present disclosure is shown in FIG. 7 and includes a body portion 114, flared widened portion 118, attachment features 112*a*, 112*b*, and a slot 116 formed in a proximal end of the body portion 114 which extends into the widened portion 118. Protrusions 114*p*1, 114*p*2, 114*p*3, 114*p*4 extend from the body portion into the slot 116, forming regions of constricted slot width 116*c*1, 116*c*2, 116*c*3, 116*c*4 that lie between regions of expanded slot width 116*e*1, 116*e*2, 116*e*3, 116*e*4, 116*e*5 with the regions of constricted slot width 116*c*1, 116*c*2, 116*c*3, 116*c*4 acting as stops for the catheter handle assembly 120 (not shown) when inserted into the tubular portion 110 in a fashion analogous to that described in conjunction with FIGS. 5A-5D.

Figure 8:
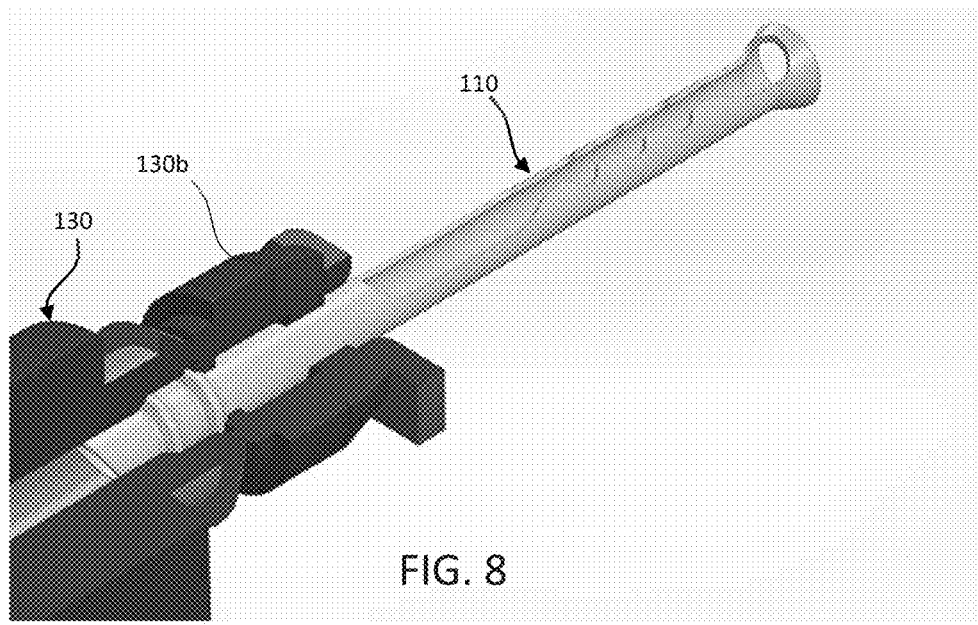
FIG. 8 is a partial cutaway perspective view of a tubular member and a proximal portion of an endoscope, in accordance with an embodiment of the present disclosure.

One or more attachment features may be configured to interface with complementary features associated with the endoscope. For example, one or more circumferential features selected from one or more circumferential protrusions and/or one or more circumferential recesses may be provided, which may interface with one or more complementary circumferential features associated with the endoscope and which may be selected from one or more complementary circumferential recesses and/or protrusions. In this regard, two circumferential protrusions may be employed as attachment features 112*a*, 112*b* as shown in FIGS. 6 and 7, which may interface with two complementary circumferential recesses associate with the endoscope. These complementary features may be formed in an entrance to a working channel of an endoscope or may be formed in another component that is configured for attachment to a working channel of an endoscope, for example, a biopsy cap 130*b* which is in turn attached to an endoscope 130 as shown in FIG. 8.

Materials for forming the tubular member 110 described herein include suitable polymers, metals, and polymer-metal composites, which provide appropriate resistance to the movement of the extension feature 122 through the regions of constricted slot width, while also providing suitable shape memory to return to an original shape after passage of the extension feature 122 through the regions of constricted slot width. Particular examples of polymers for forming the tubular member 110 include acrylonitrile butadiene styrene copolymers and polycarbonates, among other possible materials, whereas particular examples of metals for forming the tubular member 110 include elastic metals such as nitinol, among other possible materials.

Materials for forming the extension feature 122 (and also typically the shaft portion 124 and tapered region 110) include polymers, metals, and polymer-metal composites providing a stiffness sufficient to push through (i.e., spread) the regions of constricted slot width of the tubular member 110. Particular examples of materials for forming the extension feature 122 (and also typically the shaft portion 124 and tapered region 110) include metals and polymers such as acrylonitrile butadiene styrene copolymers and polycarbonates, among other possible materials.

Figure 9:
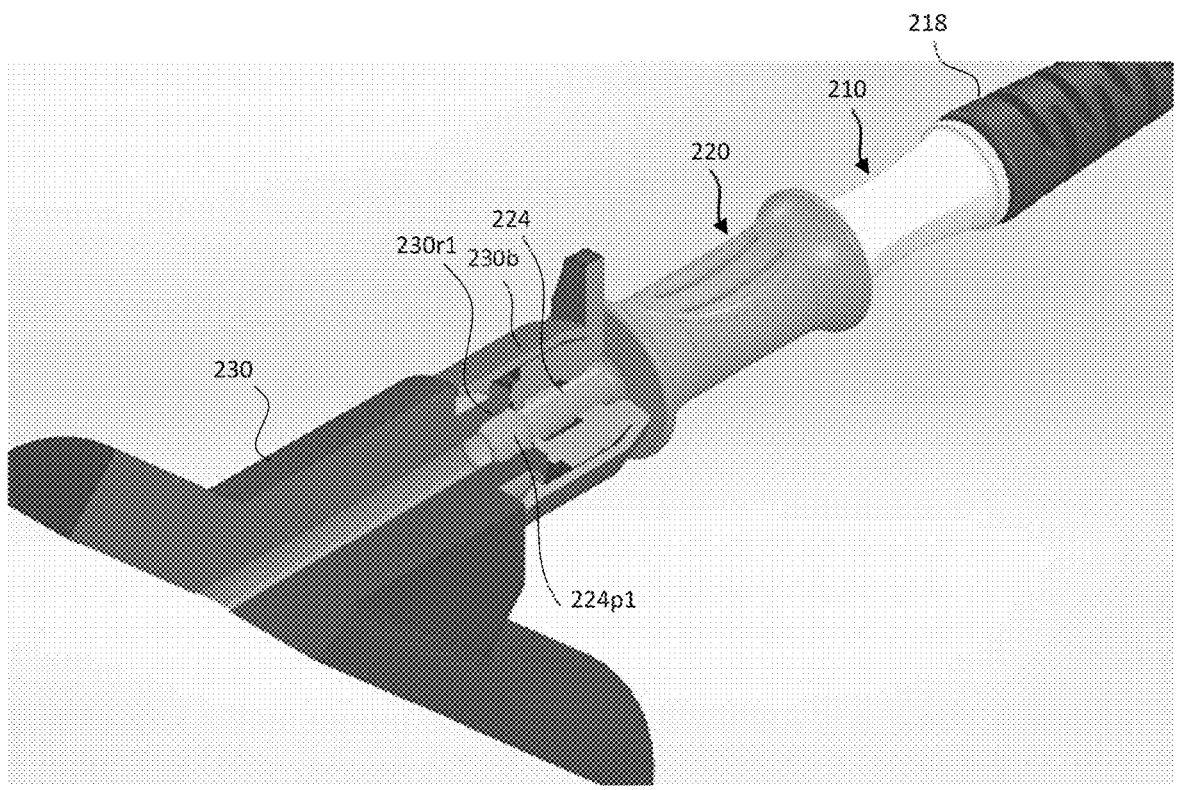
FIG. 9 is a partial cutaway perspective view of a portion of a catheter extension control assembly, in accordance with another embodiment of the present disclosure.

Alternative assemblies for controlling an amount of catheter extension will now be described. Referring now to FIG. 9 (assembled view) and FIG. 10 (exploded view), catheter extension control assembly is shown which includes an endoscope 230 with biopsy cap 230*b*, a first tubular member 210 having lumen 2101 extending therethrough, a second tubular member 220 having a lumen 2201 extending therethrough and a strain relief component 218 having a lumen 2181 extending therethrough.

The first tubular member 210 has a proximal end 210*p*, a distal end 210*d* and includes a distal sidewall portion 214 and a proximal sidewall portion 216. The strain relief component 218 is configured to be attached to the proximal end 210*p* of the first tubular member 210, and the lumens extending through the strain relief component 218 and the first tubular member 210 are configured to receive a catheter (not shown) which may be affixed to the first tubular member 210 and/or the strain relief component 218. It is noted that the assembly comprising the strain relief component 218 and first tubular member 210 is somewhat analogous to the catheter handle assembly 120 illustrated in FIG. 2. An outer surface of the distal sidewall portion 214 comprises at least one circumferential feature formed therein, which may be selected, for example, from at least one circumferential protrusion and/or at least one circumferential recess.

The second tubular member 220 has a proximal end 220*p*, and a distal end 220*d* and includes a proximal sidewall portion 222 and a distal sidewall portion 224. An outer surface of the second tubular member 220 forms a shoulder 220*s* adjacent to the distal sidewall portion 224. An inner surface of the proximal sidewall portion 222 comprises at least one circumferential feature formed therein, which may be selected, for example, from at least one circumferential protrusion and/or at least one circumferential recess, and which is complementary to the at least one circumferential feature that is formed in the outer surface of the distal sidewall portion 214. For example, with reference to FIG. 11, it can be seen that the inner surface of the proximal sidewall portion 222 of the second tubular member 220 comprises first, second and third circumferential protrusions 222*p*1, 222*p*2, 222*p*3 whereas the outer surface of the distal sidewall portion 214 of the first tubular member 210 comprises first, second and third circumferential recesses 214*r*1, 214*r*2, 214*r*3, which are complementary to the circumferential protrusions 222*p*1, 222*p*2, 222*p*3. As also seen from FIG. 11, wherein the lumen of the second tubular member 220 forms a funnel 220*f* in the proximal sidewall portion 222, with a largest diameter of the funnel located at a proximal end 220*p* of the second tubular member 220. In addition, the outer surface of the sidewall of the first tubular member 210 forms a flared configuration 210*f* that mates with the funnel 222*f*.

Figure 10:
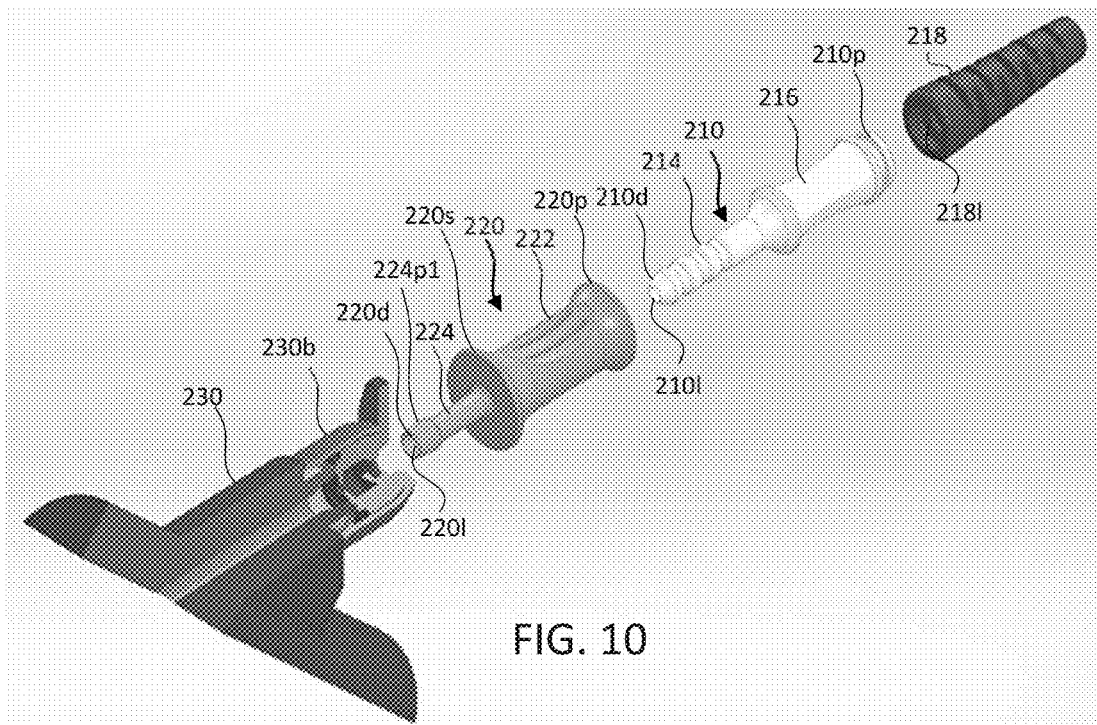
FIG. 10 is an exploded view of the catheter extension control assembly shown in FIG. 9.
Figure 11:
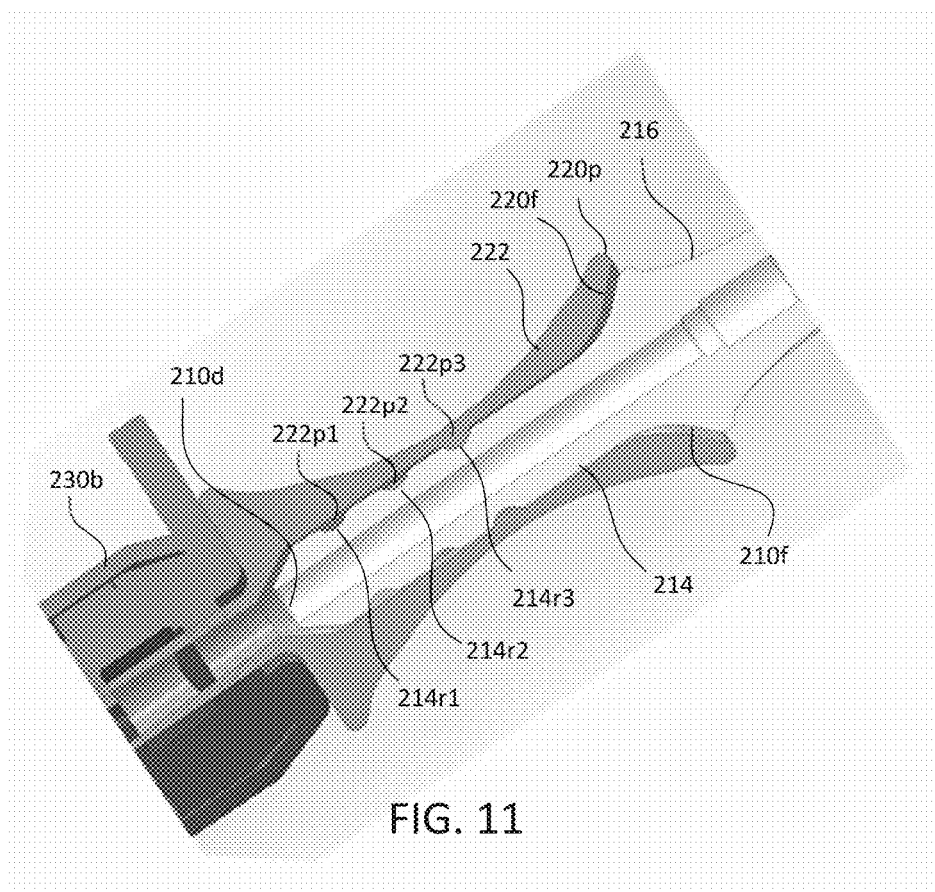
FIG. 11 is cross-sectional view a portion of the catheter extension control assembly shown in FIG. 9.

As also seen from FIGS. 9-11, the outer surface of the distal sidewall portion 224 of the second tubular member 220 may comprise at least one circumferential feature formed therein, which may be selected, for example, from at least one circumferential protrusion and/or at least one circumferential recess. An inner surface of an entrance to a working channel of the endoscope 230 (e.g., an inner surface of the biopsy cap 230*b*) may also comprise at least one circumferential feature formed therein, which is complementary to the at least one circumferential feature that is formed in the outer surface of the distal sidewall portion 224 of the second tubular member 220, and which thus may be selected, for example, from at least one circumferential protrusion and/or at least one circumferential recess. For example, with reference to FIG. 9, it can be seen that the outer surface of the distal sidewall portion 224 of the second tubular member 220 comprises a single circumferential protrusion 224*p*1 which engages a complementary circumferential recess 230r1 provided on the inner surface of the entrance to the working channel of the endoscope 230.

As can be understood by those of ordinary skill in the art with reference to FIG. 11, when the distal end 210d of the first tubular member 210 is inserted into the flared proximal end 220p of the lumen 2201 of the second tubular member 220 and advanced, the first circumferential recess 214r1 of the first tubular member 210 will initially engage (at a first stop position) the complementary third circumferential protrusion 222p3 of the second tubular member 220. Depending on the dimensions selected for the various components in this system, the first stop position may correspond to a catheter position analogous to that of FIG. 5A where a first marker band begins to emerge from a distal tip of the endoscope.

Upon further distal advancement of the first tubular member 210 relative to the second tubular member 220, the first circumferential recess 214r1 of the first tubular member 210 will engage (at a second stop position) with the complementary second circumferential protrusion 222p2 of the second tubular member 220, and the second circumferential recess 214r2 of the first tubular member 210 will engage with the complementary third circumferential protrusion 222p3 of the second tubular member 220. Depending on the dimensions selected for the various components in this system, the second stop position may correspond to a catheter position analogous to that of FIG. 5B where a second marker band begins to emerge from the distal tip of the endoscope.

Still further distal advancement of the first tubular member 210 relative to the second tubular member 220 will lead to the a third stop position having the configuration shown in FIG. 11, in which the first circumferential recess 214r1 of the first tubular member 210 is engaged with the complementary first circumferential protrusion 222p1 of the second tubular member 220, the second circumferential recess 214r2 of the first tubular member 210 is engaged with the complementary second circumferential protrusion 222p2 of the second tubular member 220, and the third circumferential recess 214r3 of the first tubular member 210 is engaged with the complementary third circumferential protrusion 222p3 of the second tubular member 220. Depending on the dimensions selected for the various components in this system, the third stop position may correspond to a catheter position analogous to that of FIG. 5C where a second marker band begins to emerge from the distal tip of the endoscope. Although not show, the first and second tubular members 210, 220 may be dimensioned such that the first tubular member 210 may be further distally advanced relative to the second tubular member 220 to a fourth stop position, which may correspond to a catheter position analogous to that of FIG. 5D.

Materials for forming the first tubular member 210 include polymers, metals, and polymer-metal composites that provide a stiffness sufficient to push the distal sidewall portion 214 of the first tubular member 210 into the lumen 2201 of the second tubular member 220. Particular examples of materials for forming the first tubular member 210 include metals and relatively stiff polymers such as acrylonitrile butadiene styrene copolymers and polycarbonates, among other possible materials.

Materials for forming the second tubular member 220 include suitable materials that that elastically accommodate movement of the distal sidewall portion 214 of the first tubular member 210 into the lumen 2201 of the second tubular member 220, while also providing suitable shape memory to return to original form such that the complementary features on the first and second tubular members 210, 220 can engage one another. Particular examples of materials for forming the second tubular member 220 include elastomeric polymers, among other possible materials.

In another embodiment, shown in FIGS. 12, 13A and 13B, a first tubular member 210 having lumen 2101 extending therethrough and a second tubular member 220 having a lumen 2201 extending therethrough are illustrated. The lumens 2101, 2201 extend through first tubular member 210 and second tubular member 220, respectively, are configured to receive a catheter (not shown) which may be affixed to the proximal end 210p of the first tubular member 210 or an additional component attached to the first tubular member 210, for example, a strain relief component analogous to that shown in FIGS. 9 and 10.

The first tubular member 210 has a proximal end 210p, a distal end 210d and includes a proximal sidewall portion 216 and a distal sidewall portion 214. An outer surface of the distal sidewall portion 214 comprises a circumferential feature in the form of a circumferential protrusion 214p. The second tubular member 220 likewise has a proximal end 220p, and a distal end 220d and includes a proximal sidewall portion 222 and a distal sidewall portion 224. An outer surface of the second tubular member 220 forms a shoulder 220s at a transition between the proximal sidewall portion 222 and the distal sidewall portion 224. As best shown in FIG. 13B, which shows a more detailed view of section 200B in FIG. 13A, an inner surface of the proximal sidewall portion 222 of the second tubular member 220 comprises a plurality of circumferential features in the form of circumferential recesses formed therein (four circumferential recesses 222r1, 222r2, 222r3, 222r4 are numbered). Each of the circumferential recesses in the inner surface of the proximal sidewall portion 222 is complementary in shape to the circumferential protrusion 214p that is formed in the outer surface of the distal sidewall portion 214 of the first tubular member 210. As also seen from FIGS. 12, 13A and 13B, the lumen of the second tubular member 220 forms a funnel 220f in the proximal portion sidewall 222, with a largest diameter of the funnel 220f located at a proximal end 220p of the second tubular member 220. In addition, the outer surface of the sidewall of the first tubular member 210 forms a flared configuration 210f that mates with the funnel 220f.

As can be understood by those of ordinary skill in the art, and with reference to FIGS. 12, 13A and 13B, when the distal end 210d of the first tubular member 210 is inserted into the flared lumen 2201 at the proximal end 220p of the second tubular member 220 and advanced, the circumferential protrusion 214p of the first tubular member 210 will initially engage the complementary first circumferential recess 222r1 of the second tubular member 220 at a first stop position. Upon, further advancement of the first tubular member 210 within the second tubular member 220, (a) the circumferential protrusion 214p of the first tubular member 210 will engage the complementary second circumferential recess 222r2 of the second tubular member 220 at a second stop position, (b) followed by engagement of the circumferential protrusion 214p of the first tubular member 210 with the complementary third circumferential recess 222r3 of the second tubular member 220 at a third stop position, (c) followed by engagement of the circumferential protrusion 214p of the first tubular member 210 with the complementary fourth circumferential recess 222r4 of the second tubular member 220 at a fourth stop position, (d) and so forth, until a final position of maximum insertion is reached. As previously described, when employed in conjunction with a catheter extension control assembly, the differing stop positions will correspond to differing lengths from which a catheter will extend from a distal end of an endoscope.

Figure 14A:
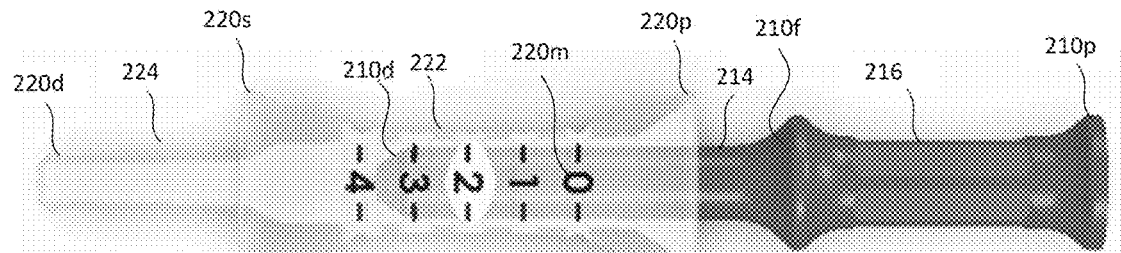
FIG. 14A is a top view of a portion of the catheter extension control assembly, in accordance with an embodiment of the present disclosure.
Figure 14B:
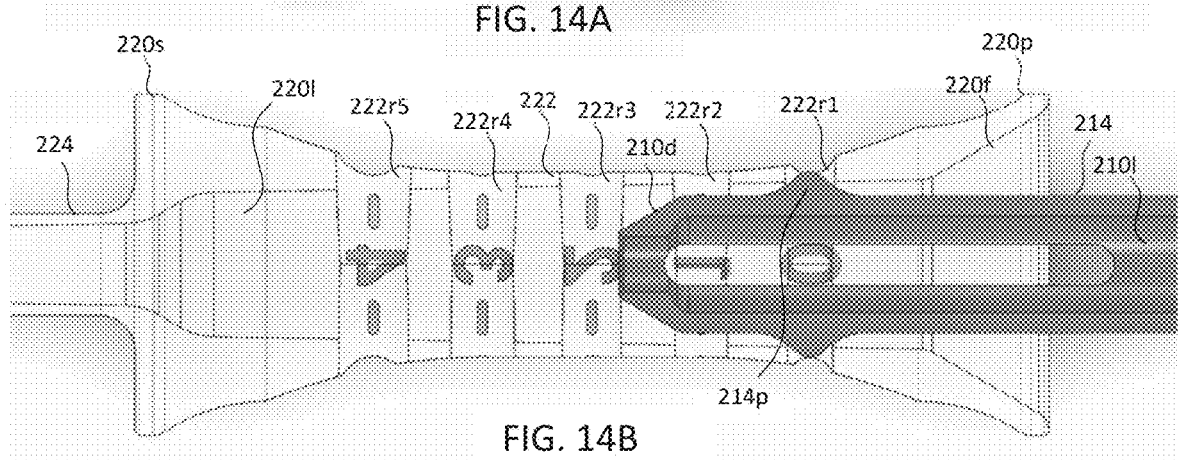
FIGS. 14B and 14C are cutaway views of a portion of a catheter extension control assembly like that shown in FIG. 14A.
Figure 14C:
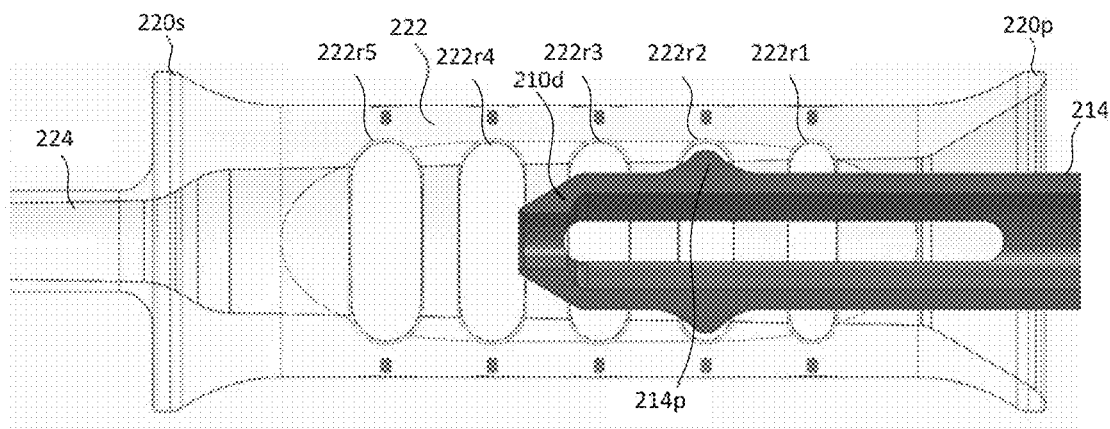

In a further embodiment shown in FIGS. 14A-14C, a first tubular member 210 having a proximal end 210p and a distal end 210d, and a second tubular member 220 having a proximal end 220p and a distal end 220d are shown. As above, lumens 2101, 2201 (see FIG. 14B) extending through first tubular member 210 and second tubular member 220 are configured to receive a catheter (not shown) which may be affixed to the proximal end 210p of first tubular member 210 or to an additional component that is attached to the first tubular member 210, for example, a strain relief component analogous to that shown in FIGS. 9 and 10.

The first tubular member 210 further includes a proximal sidewall portion 216 and a distal sidewall portion 214. An outer surface of the distal sidewall portion 214 comprises a single circumferential feature in the form of a circumferential protrusion 214p. The second tubular member 220 includes a proximal sidewall portion 222 and a distal sidewall portion 224. An outer surface of the second tubular member 220 forms a shoulder 220s at a transition between the proximal sidewall portion 216 and the distal sidewall portion 224. As best shown in FIGS. 14B-14C, an inner surface of the proximal sidewall portion 222 comprises a plurality of circumferential features in the form of circumferential recesses 222r1, 222r2, 222r3, 222r4, 222r5 formed therein. Each of the circumferential recesses 222r1, 222r2, 222r3, 222r4, 222r5 in the inner surface of the proximal sidewall portion 222 is shaped to receive the circumferential protrusion 214p that is formed in the outer surface of the distal sidewall portion 214 of the first tubular member 210. As also seen from FIGS. 14A-14C, the lumen 2201 of the second tubular member 220 forms a funnel 220f in the proximal portion sidewall 222, with a largest diameter of the funnel located at a proximal end 220p of the second tubular member 220. In addition, the outer surface of the sidewall of the first tubular member 210 forms a flared configuration 210f that mates with the funnel 222f.

As can be understood by those of ordinary skill in the art, with reference to FIGS. 14A-14C, when the distal end 210d of the first tubular member 210 is inserted into the flared lumen 2201 at the proximal end 220p of the second tubular member 220 and advanced, the circumferential protrusion 214p of the first tubular member 210 will initially engage, at a first stop position, the first circumferential recess 222r1 of the second tubular member 220 (see FIG. 14B). Upon, further advancement of the first tubular member 210 within the second tubular member 220, (a) the circumferential protrusion 214p of the first tubular member 210 will engage the second circumferential recess 222r2 of the second tubular member 220 at a second stop position (see FIG. 14C), (b) followed by engagement of the circumferential protrusion 214p of the first tubular member 210 with the third circumferential recess 222r3 of the second tubular member 220 at a third stop position (see FIG. 14A), (c) followed by engagement of the circumferential protrusion 214p of the first tubular member 210 with the fourth circumferential recess 222r4 of the second tubular member 220 at a fourth stop position, (d) followed by engagement of the circumferential protrusion 214p of the first tubular member 210 with the fifth circumferential recess 222r4 of the second tubular member 220 at a fifth stop position.

As seen from FIG. 14A, the distal portion 214 of the first tubular member 210 may comprise one or more first visually identifiable markings (e.g., circumferential protrusion 214p is provided with a distinguishing color in the embodiment shown, among other possibilities) and the second tubular member may be made transparent (or alternatively, suitable cut-outs may be provided), the such that a position of the one or more first visually identifiable markings within the second tubular member 220 may be seen. Moreover, the proximal end 222 of the second tubular member 220 may comprise a plurality of second visually identifiable markings at differing longitudinal positions which allow a user to identify the relative longitudinal position of the first tubular member 210 within the second tubular member 220. For example, second tubular member 220 may be provided with visually identifiable markings 220m that distinguish the stops from one another, for example, by employing one or more alphanumeric characters (numerals are employed in FIG. 14A). When employed in conjunction with a catheter extension control assembly, the differing stop positions will correspond to differing lengths from which a catheter will extend from a distal end of an endoscope, as previously discussed.

In other embodiments of the present disclosure, a position of a catheter may be reversibly locked relative to an endoscope. In this regard, and turning to FIG. 15, a first tubular member 210 having an axis A, a proximal end 210p and a distal end 210d, and a second tubular member 220 having an axis A (sharing a mutual axis A in FIG. 5), a proximal end 220p and a distal end 220d are shown. As in the embodiments of FIGS. 9 to 14C above, lumens 2101, 2201 extend through the first tubular member 210 and the second tubular member 220, respectively, and are configured to receive a catheter (not shown) which may be affixed to the proximal end 210p of first tubular member 210 or to an additional component attached to the first tubular member 210, for example, a strain relief component analogous to that shown in FIGS. 9 and 10.

The first tubular member 210 includes a proximal portion 216 that is provided with one or more actuators 217. The first tubular member 210 also includes a distal portion 214 that is provided with one or more radially expandable and contractible engagement members 219 (e.g., pads) which can be radially expanded and contracted by operation of the one or more actuators 217, which are configured to actuate the engagement members 219 between a radially expanded position and a radially contracted position.

For example, radially inward movement of the one or more actuators 217 may place the one or more engagement members 219 in a first position in which the engagement members 219 are radially contracted, whereas radially outward movement of the one or more actuators 217 may place the one or more engagement members 219 in a second position in which the engagement members 219 are radially expanded. In certain embodiments, one or more springs (not shown) may be used to bias the one or more actuators 217 radially outward, thereby placing the one or more engagement members 219 in the second position as a default position and requiring radially inward compression of the one or more actuators 217 to move the one or more engagement members 219 radially inward (or vice versa).

As another example, the one or more actuators 217 may be slidable longitudinally such that proximal movement of the one or more actuators 217 may place the one or more engagement members 219 in a first position in which the engagement members 219 are radially contracted, whereas distal movement of the one or more actuators 217 may place the one or more engagement members 219 in a second position in which the engagement members 219 are radially expanded. In certain of these embodiments, one or more springs (not shown) may be used to bias the one or more engagement members 219 in the second position as a default position and requiring a proximal force to be exerted on the one or more actuators 217 to move the one or more engagement members 219 radially inward (or vice versa).

Conversely, the one or more actuators 217 may be slidable longitudinally such that distal movement of the one or more actuators 217 may place the one or more engagement members 219 in a first position in which the engagement members 219 are radially contracted, whereas proximal movement of the one or more actuators 217 may place the one or more engagement members 219 in a second position in which the engagement members 219 are radially expanded. In certain of these embodiments, one or more springs (not shown) may be used to bias the one or more engagement members 219 in the second position as a default position, requiring a distal force to be exerted on the one or more actuators 217 to move the one or more engagement members 219 radially inward (or vice versa).

The second tubular member 220, on the other hand, includes a proximal sidewall portion 222 and a distal sidewall portion 224. An outer surface of the second tubular member 220 forms a shoulder 220s at a transition between proximal sidewall portion 222 and distal sidewall portion 224. At least a portion 22010 of a length of the lumen 2201 of the second tubular member 220 is of substantially constant axial cross-section (typically circular in axial cross-section). Moreover, in the embodiment shown, a funnel is formed in a proximal portion 2201p of the lumen 2201 of the second tubular member 220, with a largest diameter of the funnel located at a proximal end 220p of the second tubular member 220. In addition, an outer surface of the first tubular member 210 lying proximal to a distal portion 214 of the first tubular member 210 forms a flared configuration 210f that mates with the funnel.

Examples of materials that may be used to construct the first tubular member 210 and second tubular member 222 metals and polymers such as acrylonitrile butadiene styrene copolymers and polycarbonates, among other possible materials. Examples of materials that may be used to construct the engagement members 219 include various elastomers known in the art.

When the distal portion 214 of the first tubular member 210 is inserted into the proximal portion 222 of the second tubular member 220, so long as the one or more engagement members 219 of the first tubular member 210 are placed in a radially contracted first position wherein the one or more engagement members 219 do not engage the proximal sidewall portion 222 of the second tubular member 220, the first tubular member 210 will be freely movable relative to the second tubular member 220 over a range of longitudinal positions. On the other hand, once the one or more engagement members 219 of the first tubular member 210 are placed in a radially expanded second position such that the one or more engagement members 219 engage the proximal sidewall portion 222 of the second tubular member 220, relative longitudinal movement between the first tubular member 210 and the second tubular member 220 is resisted/prevented. Once the one or more engagement members 219 are again placed in a radially contracted first position, the first tubular member 210 will again be freely movable longitudinally relative to the second tubular member 220.

When employed in conjunction with a catheter extension control assembly, the configuration described provides a range of differing lengths that a catheter may be extended from a distal end of an endoscope. If desired, analogous to the embodiment of FIGS. 14A-14C, the distal portion 214 of the first tubular member 210 may comprise one or more first visually identifiable markings (not shown) and the second tubular member 220 may be configured (e.g., may be made transparent, may be provided with cut-out portions, etc.) such that the position of the one or more first visually identifiable markings of the first tubular member 210 can be seen within the second tubular member 220. Moreover, the proximal end 222 of the second tubular member 220 may comprise a plurality of second visually identifiable markings (e.g., one or more alphanumeric characters) (not shown) at differing longitudinal positions which allow a user to identify the relative longitudinal position of the first tubular member 210 within the second tubular member 220. The plurality of second visually identifiable markings may correspond to different lengths of catheter extension beyond a distal end of an endoscope.

Although various embodiments are specifically illustrated and described herein, it will be appreciated that modifications and variations of the present disclosure are covered by the above teachings and are within the purview of the appended claims without departing from the spirit and intended scope of the disclosure.

What is claimed is:

1. A catheter extension control assembly comprising:
  a first interior tubular member comprising a proximal portion, a distal portion, a lumen, and a sidewall having an inner surface and an outer surface at least partially surrounding the lumen, wherein the first interior tubular member is a tubular portion of a catheter or is configured to be attached to a catheter that is received in the lumen of the first interior tubular member, the catheter comprising a distal end, and wherein the outer surface of the sidewall of the first interior tubular member comprises at least one circumferential protrusion;
  a second exterior tubular member having a length, a proximal portion, a distal portion configured with an endoscope, a lumen extending the length of the second exterior tubular member, and a sidewall having an inner surface and an outer surface at least partially surrounding the lumen, wherein the lumen within the proximal portion of the second exterior tubular member is configured to slidably receive at least the distal portion of the first interior tubular member, and wherein the inner surface of the sidewall of the proximal portion of the second exterior tubular member comprises at least one circumferential recess extending into the sidewall of the second exterior tubular member at a width at least wider than the lumen of the second exterior tubular member, the at least one circumferential recess:
    configured to mate with the at least one circumferential protrusion in the outer surface of the sidewall of the first interior tubular member such that the at least one circumferential protrusion extends to the width into the circumferential recess, and
    positioned at a location on the second exterior tubular member so that, when the at least one circumferential protrusion in the first interior tubular member mates with the circumferential recess, the distal end of the catheter is positioned a predetermined minimum distance away from the endoscope at the distal portion of the second exterior tubular member; and
  a cryogen delivery catheter received in the lumen of the first interior tubular member, wherein the first interior tubular member is attached to the cryogen delivery catheter.

2. The catheter extension control assembly of claim 1, wherein the first interior tubular member comprises a plurality of the at least one circumferential protrusions and the second exterior tubular member comprises a plurality of complementary recesses of the at least one circumferential recess or wherein the first interior tubular member comprises a single circumferential protrusion of the at least one circumferential protrusion and the second exterior tubular member comprises a plurality of complementary recesses of the at least one circumferential recess.

3. The catheter extension control assembly of claim 1, wherein at least one of the first interior and second exterior tubular members comprises an elastomeric material.

4. The catheter extension control assembly of claim 1, wherein a diameter of the lumen in the proximal portion of the second exterior tubular member is greater than a diameter of the lumen in the distal portion of the second exterior tubular member.

5. The catheter extension control assembly of claim 4, wherein the outer surface of the sidewall in the proximal portion of the first interior tubular member has a diameter that is larger than a diameter of the lumen in the proximal portion of the second exterior tubular member.

6. The catheter extension control assembly of claim 4, wherein a diameter of the outer surface of the sidewall in the distal portion of the first interior tubular member is smaller than the diameter of the lumen in the proximal portion of the second exterior tubular member.

7. The catheter extension control assembly of claim 4, wherein the outer surface of the sidewall of the first interior tubular member forms a flared configuration comprising a distal concave portion extending to a radially outermost portion of the at least one circumferential protrusion and a proximal concave portion extending to the radially outermost portion of the at least one circumferential protrusion.

8. The catheter extension control assembly of claim 7, wherein the lumen of the second exterior tubular member forms a funnel in the proximal portion, with a largest diameter of the funnel located at a proximal end of the second exterior tubular member and an interior of the funnel having a shape configured to mate with the distal concave portion of the flared configuration of the outer surface of the sidewall of the first interior tubular member.

9. The catheter extension control assembly of claim 1, wherein the outer surface of the sidewall of the second exterior tubular member forms a shoulder adjacent to the distal portion of the second exterior tubular member.

10. The catheter extension control assembly of claim 1, wherein the outer surface of the distal portion of the first interior tubular member comprises one or more identifiable first markings and wherein the proximal portion of the second exterior tubular member is configured such that a position of the one or more identifiable first markings within the proximal portion of the second exterior tubular member can be seen.

11. The catheter extension control assembly of claim 10, wherein the proximal portion of the second tubular member is at least partially transparent such that the position of the one or more identifiable first markings of the first interior tubular member can be seen and wherein the proximal portion of the second exterior tubular member optionally comprises a plurality of identifiable second markings at differing longitudinal positions configured to identify a relative longitudinal position of the first interior tubular member relative to the second exterior tubular member.

12. A catheter extension control assembly comprising:
a first interior tubular member comprising a proximal portion, a distal portion, a lumen, and a sidewall having an outer surface at least partially surrounding the lumen, wherein the first interior tubular member is a tubular portion of a catheter or is configured to be attached to a catheter that is received in the lumen of the first interior tubular member, the catheter comprising a distal end, the first interior tubular member including at least one first attachment feature in said outer surface;
a second exterior tubular member having a length, a proximal portion, a distal portion configured with an endoscope, a lumen extending the length of the second exterior tubular member, and a sidewall having an inner surface and an outer surface at least partially surrounding the lumen of the second exterior tubular member, wherein at least a portion of the lumen of the second exterior tubular member is configured to receive at least a portion of the first interior tubular member, and wherein the inner surface of the sidewall of the second exterior tubular member comprises at least one second attachment feature that is complimentary to the first attachment feature, the at least one second attachment feature positioned at a location on the second exterior tubular member so that, when the at least one first attachment feature in the first interior tubular member mates with the at least one second attachment feature, the distal end of the catheter is positioned a predetermined minimum distance away from the endoscope at the distal portion of the second exterior tubular member; and
a cryogen delivery catheter received in the lumen of the first interior tubular member, wherein the first interior tubular member is attached to the cryogen delivery catheter.

13. The catheter extension control assembly of claim 12, wherein the first interior tubular member comprises a plurality of the first attachment features and the second exterior tubular member comprises one second attachment feature, or wherein the first interior tubular member comprises one first attachment feature and the second exterior tubular member comprises a plurality of the second attachment features.

14. The catheter extension control assembly of claim 12, wherein the outer surface of the sidewall of the second exterior tubular member forms a shoulder adjacent to the distal portion of the second exterior tubular member.

15. The catheter extension control assembly of claim 12, wherein a diameter of the lumen in the proximal portion of the second exterior tubular member is greater than a diameter of the lumen in the distal portion of the exterior second exterior tubular member.

16. The catheter extension control assembly of claim 15, wherein the outer surface of the sidewall in the proximal portion of the first interior tubular member has a diameter that is larger than a diameter of the lumen in the proximal portion of the second exterior tubular member.

17. The catheter extension control assembly of claim 16, wherein a diameter of the outer surface of the sidewall in the distal portion of the first interior tubular member is smaller than the diameter of the lumen in the proximal portion of the second exterior tubular member.

18. The catheter extension control assembly of claim 12, wherein the outer surface of the sidewall of the first interior tubular member forms a flared configuration comprising a distal concave portion extending to a radially outermost portion of the at least one circumferential protrusion and a proximal concave portion extending to the radially outermost portion of the at least one circumferential protrusion.

19. The catheter extension control assembly of claim 18, wherein the lumen of the second exterior tubular member forms a funnel in the proximal portion, with a largest diameter of the funnel located at a proximal end of the second exterior tubular member and an interior of the funnel having a shape configured to mate with the distal concave portion of the flared configuration of the outer surface of the sidewall of the first interior tubular member.

\* \* \* \* \*